United States Patent
Bissigner et al.

(12)

(10) Patent No.: US 6,852,822 B1
(45) Date of Patent: Feb. 8, 2005

(54) HYDROLYZABLE SILANES AND POLYMERIZABLE SILANES WITH LOW VISCOSITY AND USE THEREOF

(75) Inventors: Peter Bissigner, Diessen (DE); Oswald Gasser, Seefeld (DE); Rainer Guggenberger, Herrsching (DE); Wolfgang Soglowek, Diessen-Obermühlhausen (DE)

(73) Assignee: 3M ESPE AG, Seefeld (DE)

( * ) Notice: Subject to any disclaimer, the term of this patent is extended or adjusted under 35 U.S.C. 154(b) by 43 days.

(21) Appl. No.: 10/031,612

(22) PCT Filed: Jul. 12, 2000

(86) PCT No.: PCT/EP00/06639

§ 371 (c)(1),
(2), (4) Date: Jan. 22, 2002

(87) PCT Pub. No.: WO01/07444

PCT Pub. Date: Feb. 1, 2001

(30) Foreign Application Priority Data

Jul. 22, 1999 (DE) .......................................... 199 34 407

(51) Int. Cl.$^7$ .............................................. C08G 77/20
(52) U.S. Cl. ............................ 528/32; 528/12; 528/25; 528/41; 526/279; 106/35; 433/226; 433/217.1
(58) Field of Search .............................. 528/12, 25, 32, 528/41; 526/279; 106/35; 433/226, 217.1

(56) References Cited

U.S. PATENT DOCUMENTS

| 5,750,589 | A | 5/1998 | Zech et al. |
| 6,121,362 | A | 9/2000 | Wanek et al. |
| 6,335,413 | B1 | 1/2002 | Zech et al. |

FOREIGN PATENT DOCUMENTS

| DE | 43 39 399 A1 | 5/1995 |
| DE | 44 33 139 A1 | 3/1996 |
| DE | 197 30 515 A1 | 1/1999 |
| DE | 197 36 665 A1 | 2/1999 |
| DE | 19860361 A1 | 6/2000 |
| EP | 0 963 751 A2 | 12/1999 |
| JP | 06-228439 | * 8/1994 |
| WO | WO 94/06807 | 3/1994 |
| WO | WO 98/22521 | 5/1998 |

OTHER PUBLICATIONS

Ishikawa, Mitsuo et al., Organometallics, vol. 10, No. 8, pp. 2701–2706 (1991).
JP 07 173178 A, (Jul. 11, 1995), Abstract.
JP 11 001530 A (Jan. 6, 1999), Abstract.
Goedel, Werner et al., Am. Chem. Soc., Div. Polym. Chem., (Abstract) polymer preprint, (1997), 380, 960.

* cited by examiner

*Primary Examiner*—Kuo-Liang Peng
(74) *Attorney, Agent, or Firm*—Birch, Stewart, Kolasch & Birch, LLP

(57) ABSTRACT

The invention provides processes for making low viscosity condensates, condensates per se, and processes for making polymers from these condensates. The invention also encompasses the polymer products of these processes, especially articles for dental use. The condensates per se of the invention are of hydrolyzable silanes. The condensates can contain one or more elements selected from the group consisting of B, Al, P, Sn, Pb, the transition metals, the lanthanides and the actinides. Processes of the invention for making polymers from the condensates optionally include use of compounds that can be polymerized ionically or by radical reactions in addition to the hydrolyzable silanes. Curing of the polymers is optionally performed by photochemical, thermal or by redox-induction methods.

27 Claims, No Drawings

HYDROLYZABLE SILANES AND POLYMERIZABLE SILANES WITH LOW VISCOSITY AND USE THEREOF

This application is the national phase under 35 U.S.C. § 371 of PCT International Application No. PCT/EP00/06639 which has an International filing date of Jul. 12, 2000, which designated the United States of America.

The invention relates to hydrolyzable and polymerizable silanes with low-viscosity, processes for their preparation and their use, in particular in dental compositions.

Hydrolyzable and polymerizable silanes are known from EP-A-0 682 033 and EP-A-0 450 624 which include hydroxyl or carbonyl groups or urethane groups respectively. The molecules described there are relatively inflexible and have a high condensate viscosity which makes it necessary for example when using composite materials to use diluting monomers. However, the addition of diluting monomers has the serious disadvantage that there is the danger of an increased possibility of residual monomer release and thus of an increased toxicological unacceptability.

It is particularly necessary in the dental field to use low-viscosity and flexible molecules which do not however tend to evaporate out of the formulated compositions, as this leads to easy handling in terms of ease of removal from the storage containers and their acceptability in terms of health. Low-viscosity mixtures can also be mixed better and thereby lead to improved, more homogeneous end-products.

The object of the present invention is to provide organically modified silanes which can be hydrolyzed and polymerized and which are of low-viscosity and flexible without evaporating out of the formulated compositions, and which can thus be processed alone for example to produce dental compositions without requiring the addition of diluting monomers.

This object is achieved by hydrolyzable and polymerizable silanes of the general formula I:

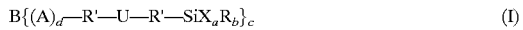

$$B\{(A)_d\text{—}R'\text{—}U\text{—}R'\text{—}SiX_aR_b\}_c \qquad (I)$$

in which the radicals and indices have the following meaning:

| | |
|---|---|
| B = | a mono- to tetravalent, straight-chained or branched organic radical with at least one C=C double bond and 4 to 50 carbon atoms; |
| X = | hydrogen, halogen, hydroxy, alkoxy, acyloxy, alkylcarbonyl, alkoxycarbonyl or $NR''_2$; |
| R = | alkyl, alkenyl, aryl, alkylaryl or arylalkyl; |
| R' = | alkylene, alkenylene, arylene, arylenealkylene or alkylenearylene each with 0 to 10 carbon atoms, these radicals being able to be interrupted by oxygen and sulphur atoms or by amino groups; |
| R'' = | hydrogen, alkyl or aryl; |
| A = | C(O)O, OC(O)O, C(O), O, S, C(O)NR'', OC(O), NR''C(O); |
| U = | an inorganically modified organic radical which contains a siloxane, carbosilane or carbosiloxane framework with at least two (siloxane, carbosiloxane) or one (carbosilane) silicon or germanium atom and contains 1 to 15 C atoms as well as up to 5 additional heteroatoms from the group O, S, N; |
| a = | 1, 2 or 3; |
| b = | 0, 1 or 2; |
| a + b = | 3; |
| c = | 1, 2, 3 or 4; |
| d = | 0 or 1. |

The silanes according to the invention are of low-viscosity and flexible and do not evaporate out of the compositions formulated with them. They can be processed alone, in mixtures or together with other hydrolyzable, condensable or polymerizable components to produce scratch-resistant coatings, filling, adhesion or sealing compounds, moulded bodies or embedding materials.

The silanes according to the invention can be universally used and can be incorporated into an inorganic-organic composite system, i.e. into an inorganic-organic network.

The distance between silicon and reactive double bond can be set as desired and the silane can also have several C=C double bonds at its disposal. Furthermore the chain between silicon and reactive double bond contains no groups capable of developing hydrogen bridges.

The silanes of formula I can be polymerized via the radicals B and hydrolyzed via the radicals X. An inorganic network with Si—O—Si units can be constructed via the hydrolyzable groups, while the double bonds contained in radical B polymerize accompanied by the construction of an organic network.

With regard to formula I and all subsequent formulae, the following definitions of radicals apply quite generally.

The alkyl radicals are for example straight-chained, branched or cyclic radicals with 1 to 20, in particular with 1 to 10 carbon atoms and preferably low alkyl radicals with 1 to 6, particularly preferably with 1 to 4 carbon atoms. Special examples are methyl, ethyl, n-propyl, i-propyl, n-butyl, s-butyl, i-butyl, t-butyl, n-pentyl, n-hexyl, cyclohexyl, 2-ethylhexyl, dodecyl and octadecyl.

The alkenyl radicals are for example straight-chained, branched or cyclic radicals with 2 to 20, preferably with 2 to 10 carbon atoms and preferably low alkenyl radicals with 2 to 6 carbon atoms, such as vinyl, allyl and 2-butenyl.

Preferred aryl radicals have 6–20, particularly preferably 6–15 carbon atoms. Preferred acyl radicals have 1–15 carbon atoms, preferably 1–10 carbon atoms. Preferred arylalkyl and alkylaryl radicals contain 7–25, preferably 7–15 carbon atoms. Preferred alkylene radicals have 2–15, particularly preferably 2 to 10 C atoms. Preferred arylene radicals have 6–25, particularly preferably 6–15 C atoms. Preferred alkylenearylene radicals have 7–25, particularly preferably 7–15 C atoms. Preferred alkoxy, acyloxy, alkylcarbonyl or alkoxycarbonyl radicals have 1–15, particularly preferably 1–10 C atoms. Preferred alkylamino and dialkylamino radicals have 1–15, particularly preferably 1–10 C atoms.

Preferred aryl radicals are phenyl, biphenyl and naphthyl. The alkoxy, acyloxy, alkylamino, dialkylamino, alkylcarbonyl, alkoxycarbonyl, arylalkyl, alkylaryl, alkylene and alkylene and alkylenearylene radicals preferably derive from the above-named alkyl and aryl radicals. Special examples are methoxy, ethoxy, n- and i-propoxy, n-, i-, s- and t-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The named radicals can optionally carry one or more substituents, for example halogen, alkyl, hydroxyalkyl, alkoxy, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, isocyanato, nitro, epoxy, $SO_3H$ or $PO_4H_2$.

Of the halogens, fluorine, chlorine and bromine and in particular chlorine are preferred.

For a=2 and b=2 respectively, the radicals X and R can each have the same or a different meaning.

The radical B derives from a mono- to tetravalent, substituted or unsubstituted compound $B((A)_dR''')_c$. $R'''$ is here an unsaturated organic radical which is suitable for the addition of SiH groups in a hydrosilylation reaction and in the process converts into the radical R'. R''' is preferably a vinyl, allyl, butenyl or higher alkenyl radical which preferably has no further substituents at the C=C double bond.

The radical B carries functional groups which are capable of polymer formation. These include in particular acrylate, methacrylate, (jointly called (meth)acrylate in the following), allyl, epoxy, oxetanyl, norbornenyl and vinylcyclopropyl groups.

Without limiting the general principle, specific representatives of radical B (in the case of methacrylates the corresponding acrylates are also always meant) are:

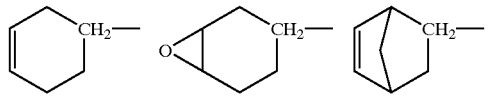

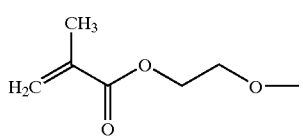

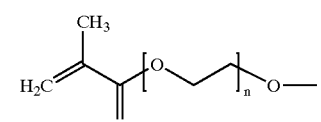

n = 2, 3, 4, 5, 6, 7 or mixtures with average n < 10

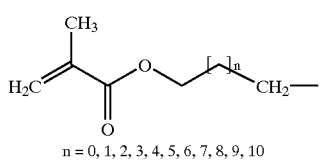

n = 0, 1, 2, 3, 4, 5, 6, 7, 8, 9, 10

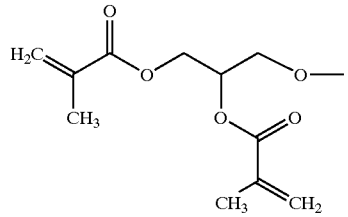

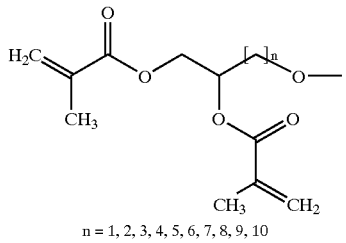

n = 1, 2, 3, 4, 5, 6, 7, 8, 9, 10

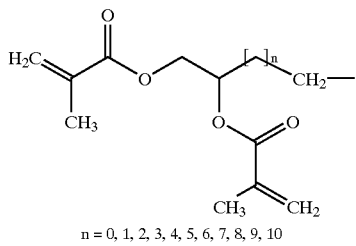

n = 0, 1, 2, 3, 4, 5, 6, 7, 8, 9, 10

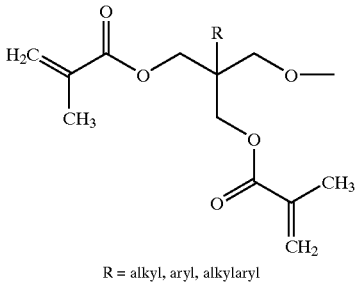

R = alkyl, aryl, alkylaryl

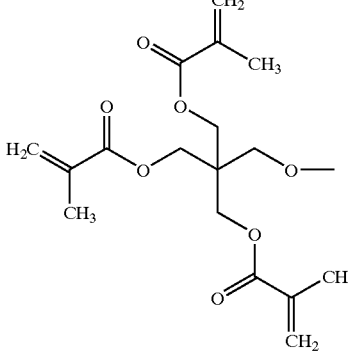

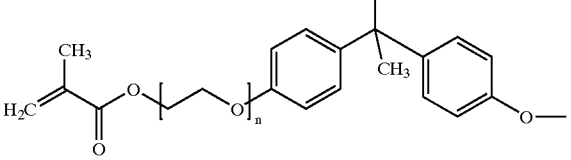

n = 1, 2, 3, 4, 5

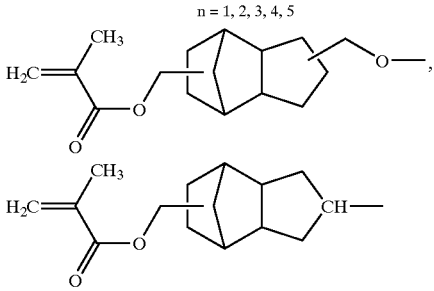

The radical B is in each case linked to a group —(A)$_n$—R'— via its free valencies.

The radical U derives from a substituted or unsubstituted compound X$_a$R$_b$Si—R'—U—H. This compound is preferably prepared by hydrosilylation from a linear di- or oligohydrido silane H—U—H and an unsaturated silicon organic compound. Here, linear means the restriction that cyclosiloxanes hydridofunctionalized at the ring are not meant. α- and β-adducts can always occur during the hydrosilylation. According to the invention the resulting mixture of the two is always meant for each hydrosilylation.

Without limiting the general principle, specific representatives of the radical U are:

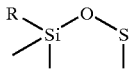 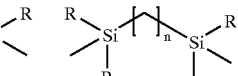

R = alkyl, aryl, cycloalkyl    R = alkyl, aryl, cycloalkyl
n = 1, 2, 3, 4, 5, 6, 7, 8, 9, 10

-continued

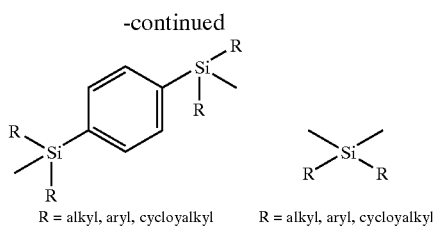

R = alkyl, aryl, cycloyalkyl      R = alkyl, aryl, cycloyalkyl

The silanes according to the invention can for example be prepared by subjecting, in a manner known per se, a C=C unsaturated silane of the general formula II:

$$R'''\text{—}SiX_aR_b \qquad (II)$$

in which X,R,a,b and a+b are as defined in claim 1 and R''', as previously mentioned, is an unsaturated organic radical which is suitable for the addition of Si—H groups in a hydrosilylation reaction and in the process changes into the radical R' according to the above definition, to an equimolar addition reaction with a compound of the general formula H—U—H, the equimolar addition product being physically separated if necessary. U has the above meaning. The equimolar addition product $$H\text{—}U\text{—}R'\text{—}Si\text{—}X_aR_b \qquad (III)$$

is changed into a derivative according to the invention by subjecting it to a further addition reaction with a compound of the general formula $B((A)_dR''')_c$. (IV) in which B,A,d,c and R''' have the meaning given above.

In the following, the synthesis principles are explained in more detail using specific reaction equations:

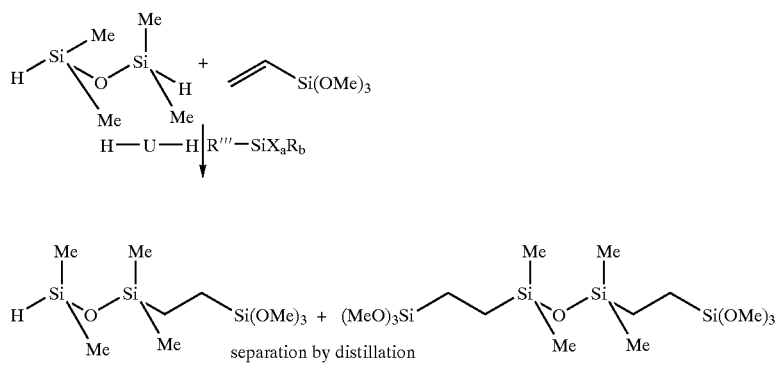

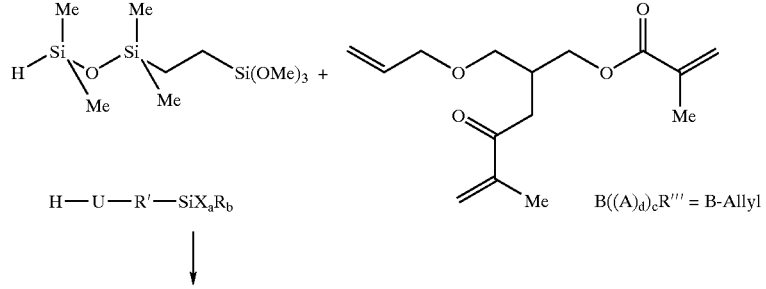

B = see structural formula; X = OMe; U = Si(Me)$_2$OSi(Me)$_2$; R''' = allyl; R' = (CH$_2$)$_2$ or CH$_2$CH(Me); a = 3; b = 0; c = 1; d = 0.

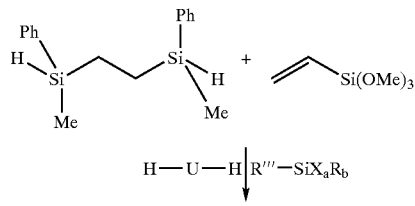

-continued

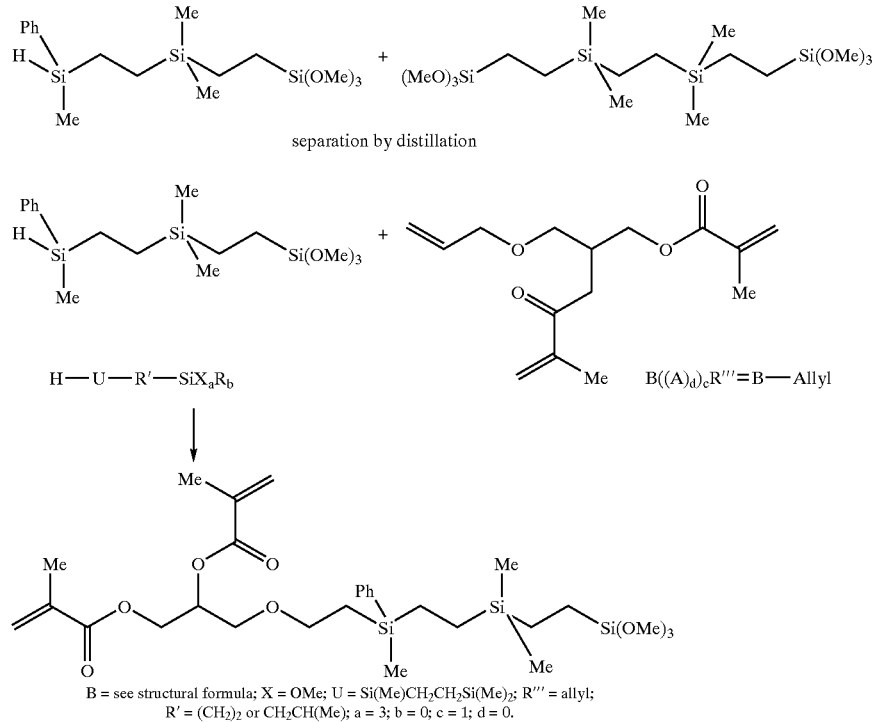

B = see structural formula; X = OMe; U = Si(Me)CH₂CH₂Si(Me)₂; R''' = allyl;
R' = (CH₂)₂ or CH₂CH(Me); a = 3; b = 0; c = 1; d = 0.

In all these reaction types, a repeated, up to quadruple, addition of the corresponding silanes to compounds B((A)$_d$R''')$_c$(IV) with c=2, 3 or 4 is possible.

Without limiting the general principle, specific examples of radicals —R'—SiX$_a$R$_b$ (formula V) are:
—(CH$_2$)$_n$—Si(CH$_3$)$_2$(OC$_2$H$_5$), with n=0 to 10
—(CH2)$_n$—Si(CH$_3$)(OC$_2$H$_5$)$_2$, with n=0 to 10
—(CH$_2$)$_n$—Si(OC$_2$H$_5$)$_3$, with n=0 to 10
—(CH$_2$)$_n$—Si(C$_2$H$_5$)$_2$(OCH3), with n=0 to 10
—(CH$_2$)$_n$—Si(C$_2$H$_5$)(OCH$_3$)$_2$, with n=0 to 10
—(CH$_2$)$_n$—Si(OC$_2$H$_5$)$_3$, with n=0 to 10
—(CH$_2$)$_n$—Si(CH$_3$)$_2$(OCH$_3$), with n=0 to 10
—(CH$_2$)$_n$—Si(CH$_3$)(OCH$_3$)$_2$, with n=0 to 10
—(CH$_2$)$_n$—Si(C$_2$H$_5$)$_2$(OC$_2$H$_5$), with n=0 to 10
—(CH$_2$)$_n$—Si(C$_2$H$_5$)(OC$_2$H$_5$)$_2$, with n=0 to 10
—(CH$_2$)$_n$—Si(CH$_3$)(C$_2$H$_5$)(OCH$_3$), with n=0 to 10
—(CH$_2$)$_n$—Si(CH$_3$)(C$_2$H$_5$)(OC$_2$H$_5$), with n=0 to 10
—(CH$_2$)$_n$—Si(CH$_3$)(OC$_2$H$_5$)(OCH$_3$), with n=0 to 10
—(CH$_2$)$_n$—Si(C$_2$H$_5$)(OC$_2$H$_5$)(OCH$_3$), with n=0 to 10
—(CH$_2$)$_n$—Si(OC$_2$H$_5$)$_2$(OCH$_3$), with n=0 to 10
—(CH$_2$)$_n$—Si(OC$_2$H$_5$)(OCH$_3$)$_2$, with n=0 to 10
—(CH$_2$)$_n$—Si(CH$_3$)(OC(CH$_3$)=CH$_2$)$_2$, with n=0 to 10
—(CH$_2$)$_n$—Si(C$_2$H$_5$)$_2$(C(CH$_3$)=CH$_2$)$_2$, with n=0 to 10
—(CH$_2$)$_n$—Si(C$_2$H$_5$)$_2$(OC(CH$_3$)=CH$_2$), with n=0 to 10
—(CH$_2$)$_n$—Si(C$_2$H$_5$)$_2$(OC(CH$_3$)=CH$_2$), with n=0 to 10
—(CH$_2$)$_n$—Si(C$_2$H$_5$)(OC(CH$_3$)=CH$_2$), with n=0 to 10
—(CH$_2$)$_n$—Si(OC$_2$H$_5$)(OC(CH$_3$)=CH$_2$)$_2$, with n=0 to 10
—(CH$_2$)$_n$—Si(OC$_2$H$_5$)$_2$(OC(CH$_3$=CH$_2$), with n=0 to 10
—(CH$_2$)$_n$—Si(OC$_2$H$_5$)$_2$(OC(CH$_3$)=CH$_2$) with n=0 to 10
—(CH$_2$)$_n$—Si(C$_6$H$_5$)(OC$_2$H$_5$)$_3$, with n=0 to 10
—(CH$_2$)$_n$—Si(C$_6$H$_5$)(OCH$_3$)$_2$, with n=0 to 10
—(CH$_2$)$_n$—Si(C$_6$H$_5$)(OCH$_3$)(OC2H$_5$) with n=0 to 10
—(CH$_2$)$_n$—Si(C$_6$H$_5$)(OC(CH$_3$)=CH$_2$)$_2$, with n=0 to 10.

The silanes according to the invention are stable compounds and can be processed either alone or together with other hydrolyzable, condensable and/or polymerizable components to produce silicic acid polycondensates or silicic acid heteropolycondensates, the definitive curing of which takes place by polymerization of the C=C double bonds.

The silanes according to the invention can however also be processed alone or together with other hydrolyzable, condensable and/or polymerizable components to produce polymerisates which can be hardened by subsequent hydrolytic condensation.

A large number of silicic acid (hetero)polycondensates which are modified with organic groups, and processes for their preparation (for example starting from hydrolytically condensable organosilanes using the sol-gel process), are known. Such condensates are used, as already mentioned at the start, for the most varied purposes, for example as moulding compounds or as lacquers for coverings. Due to the many different application possibilities of this class of substance there is however also a constant need for modification of the already known condensates, on the one hand to thereby develop new application fields and on the other hand to optimize still further their properties for certain application purposes.

The silanes according to the invention can be hydrolyzed and condensed in a basic or acid medium without a resulting linking of the C=C double bonds. It is thereby possible to incorporate the silanes according to the invention into an inorganic-organic network by hydrolytic condensation. The silanes according to the invention contain hydrolyzable groups X, for example alkoxy groups, so that an inorganic network (Si—O—Si units) can thus be built up, while the C=C double bonds contained in radical B can be polymerized accompanied by the construction of an organic network. It is thereby possible to replace organically modified, hydrolyzable and condensable silanes in coating, filling, adhesion and sealing compounds, in moulded bodies and embedding materials according to the state of the art by the silanes according to the invention.

In order to construct the inorganic network, the silanes according to the invention are hydrolyzed and polycondensed, optionally with the addition of other cocondensable components. The polycondensation preferably takes place according to the sol-gel process, as described for example in DE-A-2 758 414, DE-A-2 758 415, DE-A-3 011 761, DE-A-3 826 715 and DE-A-3 835 968.

In order to construct the organic network, the silanes according to the invention are polymerized and polycondensed optionally with the addition of other copolymerizable components. The polymerization can for example be thermal, redox-induced, covalent-nucleophilic and/or photochemical using methods such as are described for example in DE-A-3 143 820, DE-A-3 826 715 and DE-A-3 835 968.

As further polymerizable components, compounds can be added which can be radically and/or ionically polymerized. Radically polymerizable compounds which can be added are for example those with C=C double bonds, such as acrylates, vinyl cyclopropanes or methacrylates, the polymerization taking place via the C=C double bonds, optionally with the incorporation of the ring. Ionically polymerizable compounds which can be added contain for example ring systems which can be polymerized cationically in ring-opening manner, such as spiroorthoesters, spiroorthocarbonates, bicyclic spiroorthoesters, mono- or oligoepoxides or oxetanes or spirosilanes, such as are known from DE-C4 125 201.

However, compounds can also be added which can be both ionically and radically polymerized, such as methacryloyl-spiroorthoesters. These can be radically polymerized via the C=C double bond and cationically accompanied by ring opening. The preparation of these systems is described for example in Journal f. prakt. Chemie, Vol. 330, No. 2, 1988, pp. 316–318. Furthermore the silanes according to the invention can be used in systems such as are described for example in DE-A4 405 261.

Furthermore it is possible to add other known, silane-bound cyclic systems which can be jointly polymerized. Such systems are for example those which contain epoxides. Such systems are described for example in the preparation of the spirosilanes of DE-C-4 125 201.

The silanes according to the invention represent highly reactive systems which lead to poly(hetero)condensates, which for example during UV irradiation lead within a very short time to mechanically stable coverings or moulded or filling bodies. The silanes according to the invention can be prepared via simple addition reactions and can contain a variable number of reactive groups of different functionality through suitable selection of the starting compounds.

In the presence of two or more C=C double bonds in the radical B the development of a three-dimensional, organic network is possible. The mechanical properties (e.g. flexibility) and the physical-chemical properties (e.g. adsorption, refractive index, adhesion) of the poly(hetero) condensates can be influenced via the distance between the Si atom and the radical B, i.e. via the chain length, and via the presence of further functional groups in this chain. Through the development of an inorganic network, silicon- or glass-like properties of the poly(hetero)condensates can be set according to the type and number of the hydrolyzable groups (e.g. alkoxy groups).

The silanes according to the invention have relatively high molecular weights and consequently a reduced volatility vis-à-vis pure (meth)acrylate monomers, so that the toxic danger during the processing and application is less. During the inorganic and/or organic crosslinking, polysiloxanes with an again reduced volatility form which thus completely remove the toxicity problem of the acrylate components.

If the possible variations of the cocondensable and copolymerizable components are then also taken into account, it becomes clear that, via the silanes according to the invention, silicic acid (hetero)polycondensates are made available which can be adapted in many ways to given application fields and can therefore be used in all fields in which silicic acid (hetero)polycondensates have already been used, but also open up new application possibilities, for example in the field of optics, electronics, medicine, in particular dentistry, optoelectronics and packaging products for foodstuffs.

The silanes according to the invention can be used either as such or in compositions which additionally contain additives suited to the application purpose, for example customary lacquer additives, solvents, fillers, photoinitiators, thermal initiators, flow agents and pigments.

The silanes according to the invention or the compositions containing silanes are suitable for example for the preparation of coating, filling or bulk materials, of adhesives and injection-moulding compounds, of fibres, particles, films, adhesion promoters, impression compounds and embedding materials.

Coatings and moulded bodies from the silanes according to the invention have the advantage that they can be photochemically structured. Special application fields are for example the coating of substrates from metal, plastic, paper, ceramics (by immersion, pouring, painting, spraying, electrostatic spraying, electroimmersion varnishing), use for optical, optoelectric or electronic components, the production of fillers, the production of scratch-resistant, wear-resistant corrosion-protection coatings of moulded bodies, for example by injection moulding, mould casting, pressing, rapid prototyping or extrusion, and the production of composites, for example with fibres, fillers or woven fabrics.

In addition to the silanes of formula I according to the invention further hydrolytically condensable compounds of silicon, boron, aluminium, phosphorous, tin, lead, the transition metals, the lanthanides or the actinides can also be used. These compounds can be used either as such or already in precondensed form for the preparation of the polycondensates. It is preferred if at least 10 mol-%, in particular at least 80 mol-% and specially at least 90 mol-%, based on monomeric compounds, of the starting materials used for the preparation of the silicic acid (hetero)polycondensates are silicon compounds.

It is likewise preferred if at least 5 mol-%, for example 25 to 100 mol-%, in particular 50 to 100 mol-%, and specially 75 to 100 mol-%, of the silicic acid (hetero)polycondensates, each based on monomeric compounds, are based on one or more of the silanes according to the invention.

Of the hydrolytically condensable silicon compounds, different from the silanes of general formula I, which can optionally be used, those of the general formula VI are particularly preferred:

$$R_a(R^{10}Z')_f SiX_{4-(e+f)} \tag{VI}$$

in which the individual radicals R, $R^{10}$, X and Z' are the same or different, the radicals R and X are as defined above and the radicals $R^{10}$ and Z' and the indices e and f have the following meaning:

$R^{10}$=alkylene or alkenylene, these radicals being able to be interrupted by oxygen or sulphur atoms or —NH groups;

Z'=halogen or an optionally substituted amino, amide, aldehyde, alkylcarbonyl, carboxy, mercapto, cyano, alkoxy, alkoxycarbonyl, sulfonic acid, phosphoric acid, acryloxy, methacryloxy, epoxy or vinyl group;

e=0,1,2 or 3;

f=0,1,2 or 3, with e+f=1,2 or 3.

Such silanes are described for example in DE-C-34 07 087.

Special examples for hydrolytically condensable silanes of the general formula VI are:

$CH_3$—Si—$Cl_3$, $CH_3$—Si—$(OC_2H_5)_3$, $C_2H_5$—Si—$Cl_3$, $C_2H_5$—Si—$(C_2H_5)_3$, $CH_2$=CH—Si—$(OC_2H_5)_3$, $CH_2$=CH—Si$(OC_2H_4OCH_3)_3$, $(CH_3)_2$—Si—$Cl_2$,

CH$_2$=CH—Si—(OOCCH$_3$)$_3$, (CH$_3$)$_2$—Si—(OC$_2$H$_5$)$_2$, (C$_2$H$_5$)$_3$—Si—Cl, (C$_2$H$_5$)$_2$—Si—(OC$_2$H$_5$)$_2$, (CH$_3$)$_2$(CH$_2$=CH)—Si—Cl$_2$, (CH$_3$)$_3$—Si—Cl, (t-C$_4$H$_9$)(CH$_3$)$_2$—Si—Cl, (CH$_3$O)$_3$—Si—C$_3$H$_5$—NH—C$_2$H$_4$—NH—C$_2$H$_4$—NH$_2$, (CH$_3$O)$_3$—Si—C$_3$H$_6$—SH, (CH$_3$O)$_3$—Si—C$_3$H$_6$—NH—C$_2$H$_4$—N H$_2$, (CH$_3$O)$_3$—Si—C$_3$H$_6$—Cl, (CH$_3$O)$_3$—Si—C$_3$H$_5$—O—C(O)—C(CH$_3$)=CH$_2$, (CH$_3$)$_2$(CH$_2$=CH—CH$_2$)—Si—Cl, (C$_2$H$_5$O)$_3$—Si—C$_3$H$_6$—NH$_2$, (C$_2$H$_5$O)$_3$—Si—C$_3$H$_6$CN,

The silanes according to the invention need not necessarily be specially isolated for the further processing to poly(hetero)condensates. It is also possible to prepare these silanes in a one-pot process first and then optionally after adding further hydrolyzable compounds hydrolytically condense them.

Of the hydrolytically condensable silicon compounds, different from the silanes of general formula I, which can optionally also be used, those of the general formula VIII are likewise particularly preferred:

$$Y_n SiX_m R_{4-(n+m)} \quad (VIII)$$

in which the individual radicals X, Y and R are in each case the same or different and X and R have the above, and Y, n and m the following, meaning:

Y+a substituent, which contains a substituted or unsubstituted 1,4,6-trioxaspiro-[4,4]-nonane radical;
n=1,2 or 3;
m=1,3 or 3, or with m+n≦4.

These spirosilanes can be hydrolyzed via the radicals X and polymerized via the radicals Y and are described in great detail in DE-C4 125 201.

Of the hydrolytically condensable silicon compounds, different from the silanes of general formula I, which can optionally be used, those of the general formula IX are likewise preferred:

$$G\{A—(Z)_d—R^{20}(R^{21})—R'—SiX_a R_b\}_c \quad (IX)$$

in which the radicals X, R and R' have the above meaning and the other radicals and indices have the following meaning:

| | |
|---|---|
| G = | a mono- to tetravalent, straight-chained or branched organic radical with at least one C=C double bond and 4 to 50 carbon atoms; |
| A = | O, S or NH for d = 1 and |
| Z = | CO and |
| R$^{20}$ = | alkylene, arylene or alkylenearylene in each case with 1 to 10 carbon atoms, these radicals being able to be interrupted by oxygen and sulphur atoms or by amino groups, and |
| R$^{21}$ = | COOH; |
| or | |
| A = | O, S or NH for d = 1 and |
| Z = | CO and |
| R$^{20}$ = | alkylene, arylene or alkylenearylene in each case with 1 to 10 carbon atoms, these radicals being able to be interrupted by oxygen and sulphur atoms or by amino groups, and |
| R$^{21}$ = | H; |
| or | |
| A = | O, S, NH or COO for d = 1 and |
| Z = | CHR, with R equal to H, alkyl, aryl or alkylaryl, and |
| R$^{20}$ = | alkylene, arylene or alkylenearylene in each case with 1 to 10 carbon atoms, these radicals each being able to be interrupted by oxygen and sulphur atoms or by amino groups, and |
| R$^{21}$ = | OH; |
| or | |
| A = | O, S, NH or COO for d = 0 and |
| R$^{20}$ = | alkylene, arylene or alkylenearylene in each case with 1 to 10 carbon atoms, these radicals being able to be interrupted by oxygen and sulphur atoms or by amino groups, and |
| R$^{21}$ = | OH; |
| or | |
| A = | S for d = 1 and |
| Z = | CO and |
| R$^{20}$ = | N and |
| R$^{21}$ = | H; |
| a = | 1, 2 or 3; |
| b = | 0, 1 or 2; |
| a + b = | 3; |
| c = | 1, 2, 3 or 4; |
| d = | 0 or 1. |

The silanes of formula IX can be polymerized via the radicals G and hydrolyzed via the radicals X. An inorganic network with Si—O—Si units can be constructed via the hydrolyzable groups, while the double bonds contained in the radical G polymerize accompanied by the construction of an organic network.

For a=2 or b=2 the radicals X and R can in each case have the same or a different meaning.

Of the optionally used hydrolyzable aluminium compounds, those are particularly preferred which have the general formula AlR°$_3$, in which the radicals R°, which can be the same or different, are selected from halogen, alkoxy, alkoxycarbonyl and hydroxy. With regard to the more detailed (preferred) definitions of these radicals, reference can be made to the statements in connection with the suitable hydrolyzable silicon compounds. The just-named groups can also be replaced completely or partly by chelate ligands (for example acetylacetone or aceto acetic acid ester, acetic acid).

Particularly preferred aluminium compounds are aluminium alkoxides and halides. In this connection the following can be named as specific examples:

Al(OCH$_3$)$_3$, Al(OC$_2$H$_5$)$_3$, Al(O-n-C$_3$H$_7$)$_3$, Al(O-i-C$_3$H$_7$)$_3$, Al(OC$_4$H$_9$)$_3$, Al(O-i-C$_4$H$_9$)$_3$, Al(O-s-C$_4$H$_9$)$_3$, AlCl$_3$, AlCl—(OH)$_2$.

Compounds which are liquid at room temperature such as for example aluminium-sec.-butylate and aluminium-isopropylate, are particularly preferred.

Suitable hydrolyzable titanium or zirconium compounds, which can optionally be used, are those of the general formula MX$_y$R$_z$, in which M stands for Ti or Zr, y is an integer from 1 to 4, in particular 2 to 4, z stands for 0,1,2 or 3, preferably for 0, 1 or 2, and X and R are as defined in the case of the general formula I. This also applies to the preferred meanings. It is particularly preferred if y is equal to 4.

As in the case of the above Al compounds, complexed Ti or Zr compounds can also be used. Additional preferred complexing agents here are acrylic acid and methacrylic acid.

Specific examples of Zr and Ti compounds are the following:

TiCl$_4$, Ti(OC$_2$H$_5$)$_4$, Ti(OC$_3$H$_7$)$_4$, Ti(O-i-C$_3$H$_7$)$_4$, Ti(OC$_4$H$_9$)$_4$, Ti(2-ethylhexoxy)$_4$, ZrCl$_4$, Zr(OC$_2$H$_5$)$_4$, Zr—(OC$_3$H$_7$)$_4$, Zr(O-i-C$_3$H$_7$)$_4$, Zr(OC$_4$H$_9$)$_4$, Zr(2-ethylhexoxy)$_4$, ZrOCl$_2$.

Further hydrolyzable compounds which can be used for the preparation of the polyheterocondensates are for example boron trihalides and boric acid esters, such as BCl$_3$, B(OCH$_3$)$_3$ and B(OC$_2$H$_5$)$_3$, stannous tetrahalides and stannous tetraalkoxides, such as SnCl$_4$ and Sn(OCH$_3$)$_4$, and vanadyl compounds, such as VOCl$_3$ and VO(OCH$_3$)$_3$.

As already mentioned, the preparation of the poly(hetero) condensates can take place in a manner customary in this field. If silicon compounds are used practically exclusively, the hydrolytic condensation can in most cases take place by adding the necessary water directly to the silicon compounds to be hydrolyzed, which are present either as such or dissolved in a suitable solvent, at room temperature or accompanied by slight cooling (preferably while stirring and in the presence of a hydrolysis and condensation catalyst) and thereupon stirring the resulting mixture for some time (one to several hours).

In the presence of reactive compounds of Al, Ti or Zr, a step-by-step addition of the water is recommended as a rule. Regardless of the reactivity of the compounds present, the hydrolysis takes place as a rule at temperatures between –20 and 130° C., preferably between 0 and 30° C. or the boiling point of the optionally used solvent. As already pointed out, the best method of adding water depends above all on the reactivity of the starting compounds used. Thus, for example, the dissolved starting compounds can be dropped slowly to an excess of water, or water is added in a portion or portionwise to the optionally dissolved starting compounds. It can also be useful not to add the water as such, but to introduce it into the reaction system with the help of hydrous organic or inorganic systems. In many cases, the introduction of the quantity of water into the reaction mixture with the help of moisture-laden absorbents, for example molecular sieves and hydrous organic solvents, for example 80% ethanol, has proved particularly suitable. The addition of water can however also take place via a chemical reaction in which water is released in the course of the reaction. Examples of this are esterifications.

If a solvent is used, consideration is also given, in addition to the low aliphatic alcohols (for example ethanol or i-propanol), to ketones, preferably low dialkylketones, such as acetone or methyl isobutyl ketone, ethers, preferably low dialkylethers such as diethylether or dibuylether, THF, amides, esters, in particular acetic acid ethyl ester, dimethylformamide, amines, in particular triethylamine, and their mixtures.

If spirosilanes are used for the preparation of the poly (hetero)condensates then the hydrolysis is preferably carried out in a medium which is basic with regard to the spirosilanes. This is produced either by a basic solvent, such as for example triethylamine, or by adding basic hydrolysis and condensation catalysts, such as KOH, methylimidazole.

The starting compounds need not necessarily already all be present at the start of the hydrolysis (polycondensation), but in certain cases it can even prove to be advantageous if only some of these compounds are firstly brought into contact with water and the remaining compounds are added later.

In order to avoid precipitations during hydrolysis and polycondensation as much as possible, in particular when using hydrolyzable compounds different from silicon compounds, the addition of water can be carried out in several steps, for example in three steps. In the first step, a tenth to a twentieth of the amount of water required for hydrolysis can for example be added. After brief stirring, a fifth to a tenth of the required amount of water can be added, and after further brief stirring, the remainder can finally be added.

The condensation time is geared to the starting components in each case and their proportions, to the optionally used catalyst, to the reaction temperature, etc. In general, the polycondensation takes place under normal pressure, but can also be carried out at increased or reduced pressure.

The thus-obtained poly(hetero)condensate can be processed further either as such or after partial or almost complete removal of the solvent used. In some cases it can prove to be advantageous in the product obtained after the polycondensation to replace the excess water and the formed and optionally additionally used solvent with another solvent, in order to stabilize the poly(hetero)condensate. For this purpose, the reaction mixture can be thickened for example under vacuum at a slightly increased temperature to the point where it can still be taken up problem-free by another solvent.

If these poly(hetero)condensates are to be used as lacquers for coating (for example of plastics such as PVC, PC, PMMA, PE, PS of glass, paper, wood, ceramics, metal etc), then customary lacquer additives, such as colouring agents (pigments or dyes), fillers, oxidation inhibitors, flame-protection products, flow agents, UV adsorbers, stabilizers or similar, can optionally also be added to them at the latest before use. Additives to increase conductivity (for example graphite powder, silver powder) also merit a mention in connection with this. In the case of use as moulding compound, the addition of inorganic and/or organic fillers, such as organic and inorganic particles, (glass) fibres, minerals, can in particular be considered.

The final curing of the poly(hetero)condensates takes place after the addition of suitable initiators, and is thermal, redox-induced, covalent-nucleophilic or photochemical, several curing mechanisms also being able to operate in parallel and/or in sequence. In the course of the polymerization, the C=C double bonds are linked and the organic network is constructed. Due to the relatively high molecular weights of the silanes according to the invention, these experience only a slight volume shrinkage during curing.

It is also possible to add further ionically and/or radically polymerizable components to the poly(hetero)condensate before the final curing, i.e. before polymerization. Radically polymerizable compounds which can be added are for example those with C=C double bonds, such as say acrylates or methacrylates, the polymerization taking place via the C=C double bonds. Ionically polymerizable compounds which can be added contain for example ring systems which can be polymerized cationically in ring-opening manner, such as say spiroorthoesters, spiroorthocarbonates, bicyclic spiroorthoesters, mono- or oligoepoxides or spirosilanes of the general formula VIII. However, compounds can also be added which can be polymerized both cationically and radically, such as for example methacryloyl spiroorthoesters. These can be polymerized radically via the C=C double bond and cationically accompanied by ring opening. These systems are described for example in the Journal f. prakt. Chemie., Volume 330, No. 2, 1988, pp. 316–318 or in the Journal of Polymer Science: Part C, Polymer Letters, Vol. 26, pp. 517–520 (1988).

If the curing of the poly(hetero)condensate takes place photochemically, photoinitiators are added to the latter, thermal initiators in the case of thermal curing, and starter-activator systems in the case of redox-induced curing.

The initiator can be added in normal amounts. Thus, for example, there can be added to a mixture which contains 30 to 50 wt.-% solids (polycondensate), initiators in a quantity of for example 0.5 to 5 wt.-%, in particular from 1 to 3 wt.-%, relative to the mixture.

If, for the preparation of the poly(hetero)condensates, in addition to the silanes according to the invention, further components are used which contain reactive double bonds, such as silanes according to the general formula VII, then a polymerization can likewise take place via these double bonds which can be thermal and/or photochemical and/or covalent-nucleophilic and/or redox-initiated.

There can be used as photoinitiators for example those which are commercially available. Examples of these are Irgacure 184 (1-hydroxycyclohexylphenylketone), Irgacure 500 (1-hydroxycyclohexylphenylketone-benzophenone), and other Irgacure-type photoinitiators which can be obtained from Ciba-Geigy: Darocure 1173, 1116, 1398, 1174 and 1020 (obtainable from Merck), benzophenone, 2-chlorothioxanthone, 2-methylthioxanthone, 2-isopropylthioxanthone, benzoin, 4,4'-dimethoxybenzoin etc. If the curing takes place with visible light, such as for example in dentistry, camphorquinone for example can be used as initiator.

Coming into consideration as thermal initiators are in particular organic peroxides in the form of diacylperoxides, peroxydicarbonates, alkylperesters, dialkylperoxides, perketals, ketone peroxides and alkylhydroperoxides. Specific and preferred examples of thermal initiators are dibenzoyl peroxide, t-butylperbenzoate and azobisisobutyronitrile.

Starter activator systems customary for this purpose can be used, such as for example aromatic amines (for example N,N-bis-(2-hydroxyethyl)-p-toluidine) as activators, or dibenzoyl peroxide for example as starters, the curing time being able to be set according to the respective use via their concentration and/or their concentration ratio. Further amines can be found for example in DE-A4 310 733.

In the case of covalent-nucleophilic curing, compounds with at least one amino group for example are added as initiators. Suitable amines can be found for example in DE-A4 405 261.

A lacquer (poly(hetero)condensate) provided with an initiator on the basis of the silanes according to the invention can be used for coatings of substrates. Customary coating processes can be used for this coating, for example dipping, flooding, pouring, centrifuging, rolling, spraying, painting, electrostatic spraying and electrodip-coating. It should also be mentioned here that the lacquer need not necessarily contain solvent. In particular when using starting substances (silanes) with two alkoxy groups at the Si atom, it is also possible to proceed without the addition of solvents.

Before curing, the applied lacquer is preferably left to dry. Afterwards, depending on the type of initiator, it can be cured in a manner known per se by redox-initiation, thermally or photochemically. Naturally, combinations of curing methods are also possible.

If the curing of the applied lacquer takes place by irradiation it can prove advantageous to carry out a thermal curing after the radiation curing, in particular to remove solvent which is still present or to incorporate still more reactive groups into the curing.

Although polymerizable groups are already present in the poly(hetero)condensates on the basis of the silanes according to the invention, it can prove advantageous in certain cases to add still more compounds (preferably of a purely organic nature) with for example unsaturated groups to these condensates before or during their further processing (curing).

Preferred examples of such compounds are acrylic acid and methacrylic acid as well as compounds derived therefrom, in particular esters of preferably monohydric alcohols (for example $C_{1-4}$ alkanols), (meth)acrylonitrile, styrene and mixtures of same. In the case of using the poly(hetero)condensates for the preparation of coating lacquers, such compounds can act simultaneously as solvents and/or diluting agents.

The preparation of moulded bodies or moulding compounds from poly(hetero)condensates on the basis of silanes according to the invention can take place with every method customary in this field, for example by injection moulding, mould casting, extrusion. The poly(hetero)condensates based on the silanes according to the invention are also suitable for the preparation of composite materials (for example with glass-fibre reinforcement).

With the multifunctional silanes according to the invention, starting compounds are available which make possible the preparation of inorganic-organic composite polymers having the most varied properties which can be set within wide ranges, or the modification of existing composite polymers. The use of such materials extends to the most varied purposes and among others to their use as bulk materials, composites, adhesives, casting compounds, coating materials, adhesion promoters, and binders for ceramic particles (ceramic shaping processes), for the preparation or priming of fillers and fibres, grinding wheels, for use in the reaction extruder, etc. For organic polymerization, photochemically, thermally and chemically (2-component, anaerobic, redox etc) induced conversion can be considered. The combination of self-curing with for example photo-induced or thermal curing is likewise possible.

The invention is explained in the following in more detail by examples, without it thereby being limited in any way.

PREPARATION EXAMPLE 1

Preparation of the Hydrosilylation Product of 1-(trimethoxysilylethyl)-1,1,3,3-tetramethyldisiloxane with Allyloxyethyl Methacrylate

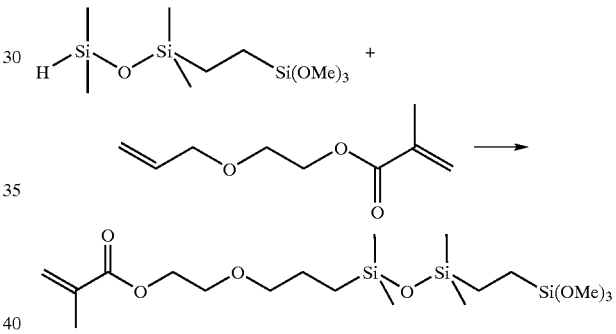

1-(trimethoxysilylethyl)-1,1,3,3-tetramethyldisiloxane was obtained from 1,1,3,3-tetramethyldisiloxane and vinyl-trimethoxysilane according to J. V. Crivello and Daoshen Bi (J. Polym. Sci A 31 (1993) 3121).

14.1 g (0.05 M) 1-(trimethoxysilylethyl)-1,1,3,3-tetramethyldisiloxane are heated to 100° C. in 100 ml dry toluene under inert gas with 5 mg of polymer-bound Wilkinson catalyst and 8.5 g (0.05 M) of allyloxyethyl methacrylate. After four hours the allyl and SiH absorptions in the $^1$H-NMR spectrum have disappeared. The reaction mixture is left to cool, filtered from the catalyst and the solvent drawn off under reduced pressure.

A colourless, low-viscosity oil remains. The yield is 98% of the theoretical value.

PREPARATION EXAMPLE 2

Hydrolysis and Condensation of the Product from Preparation Example 1

9.1 g (0.02 mol) of the compound from preparation example 1 are stirred with 1.1 g (0.06 mol) water (added as 0.1 M HCl) in 50 ml acetic ester for 24 hours at 40° C. The reaction mixture is then neutralized with NaHCO$_3$ solution, dried and freed of solvent. The condensate is capable of flowing and is obtained in a yield of 96% of the theoretical value.

PREPARATION EXAMPLE 3

Co-Hydrolysis of the Product from Example 1 with TMOS 9.1 g (0.02 mol) of the compound from preparation example 1 are reacted with 0.76 g (0.005 mol) tetramethylorthosilicate (TMOS) and agitated in 50 ml acetic ester with 1.4 g (0.08 mol) water (added as 0.1 M HCl) for 36 hours at 36° C. The solution is neutralized using NaHCO$_3$ solution, dried and freed of the solvent. The yield of viscose condensate is 95% of the theoretical value.

PREPARATION EXAMPLE 4

Preparation of the Hydrosilylation Product from 1-(trimethoxysilylethyl)-1,1,4,4-tetramethyldisilabutane and glycerol dimethyacrylate-allylether

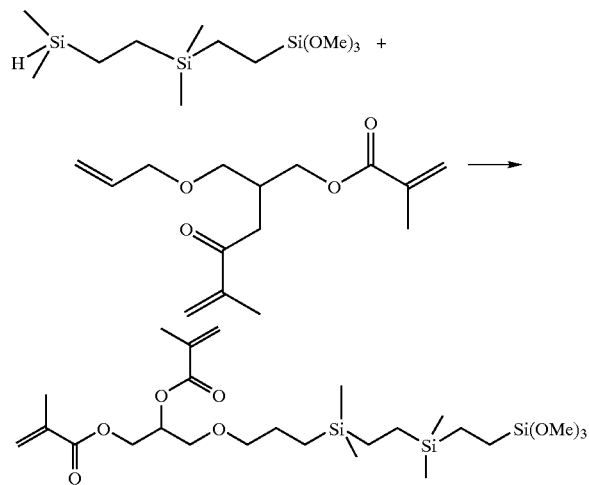

1-(trimethoxysilylethyl)-1,1,4,4-tetramethyldisilabutane is prepared analogously to 1-(trimethoxysilylethyl)-1,1,3,3-tetramethyldisiloxane in preparation example 1 from 1,2-bisdimethylsilylethane. A colourless, hydrolysis-labile oil is obtained in a yield of 54% of the theoretical value.

5.9 g (0.02 M) 1-(trimethoxysilylethyl)-1,1,4,4-tetramethyldisilabutane are dissolved in 100 ml dry toluene and reacted with 5 mg Deloxane Pt catalyst and under reflux with 5.4 g (0.02 M) glyceroldimethyacrylate-allylether. After the heat effect has faded, a sample is taken and the SiH vibration at 2160 cm$^{-1}$ tested by means of IR. When this has disappeared, the reaction mixture is filtered off from the catalyst and the solvent distilled off. The adduct is obtained as a colourless, hydrolysis-labile oil in a yield of 94% of the theoretical value.

PREPARATION EXAMPLE 5

Hydrolysis and Condensation of the Product from Preparation Example 4

11.3 g (0.02 mol) of the compound from example 4 are agitated with 1.1 g (0.06 mol) water (added as 0.1 M HCl) in 50 ml acetic ester for 24 hours at 40° C. The reaction mixture is then neutralized with NaHCO$_3$ solution, dried and freed of solvent. The condensate is capable of flowing and is obtained in a yield of 97% of the theoretical value.

PREPARATION EXAMPLE 6

Co-Hydrolysis of the Product from Preparation Example 4 with TMOS 11.3 g (0.02 mol) of the compound from example 4 are reacted with 0.8 g (0.005 mol) tetramethylorthosilicate and agitated in 50 ml acetic ester with 1.4 g (0.08 mol) water (added as 0.1 M HCl) for 36 hours at 36° C. The solution is neutralized by means of NaHCO$_3$ solution, dried and freed of solvent. The yield of viscose condensate is 96% of the theoretical value.

PREPARATION EXAMPLE 7

Preparation of the Hydrosilylation Product from 1-(trimethoxysilylethyl)-1-methyl-1-phenylsilane and glycerol dimethacrylate-allylether

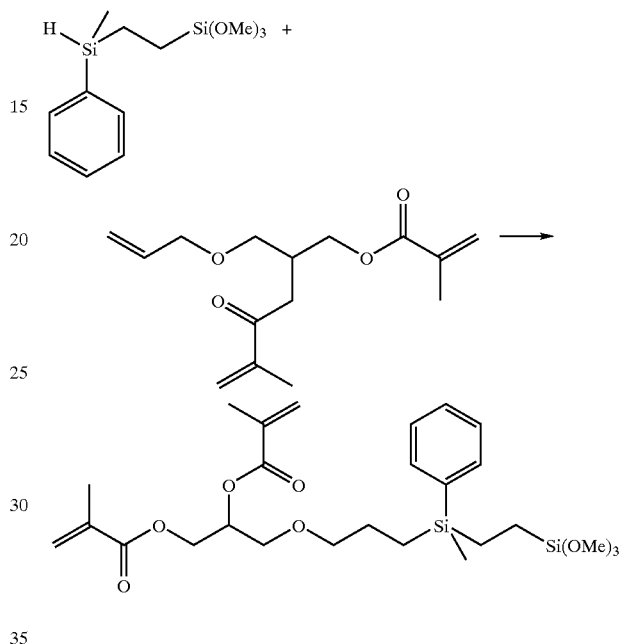

1-(trimethoxysilylethyl)-1-methyl-1-phenylsilane is prepared analogously to 1-(trimethoxysilylethyl)-1,1,3,3-tetramethyldisiloxane in preparation example 1 from 1-methyl-1-phenylsilane. It is obtained as a colourless, hydrolysis-labile oil in a yield of 69% of the theoretical value.

13.5 g (0.05 mol) 1-(trimethoxysilylethyl)-1-methyl-1-phenylsilane are dissolved in 100 ml dry toluene and reacted with 5 mg Deloxane Pt catalyst and under reflux with 13.4 g (0.05 mol) glycerol dimethacrylate-allylether. After the heat effect has faded, a sample is taken and the SiH vibration at 2160 cm$^{-1}$ tested by means of IR. If this has disappeared, the reaction mixture is filtered off from the catalyst and the solvent distilled off. The adduct is obtained as a colourless, hydrolysis-labile oil in a yield of 94% of the theoretical value.

PREPARATION EXAMPLE 8

Hydrolysis and Condensation of the Product from Preparation Example 7

10.8 g (0.02 mol) of the compound from preparation example 7 are agitated with 1.1 g (0.06 mol) water (added as 0.1 M HCl) in 50 ml acetic ester for 24 hours at 40° C. The reaction mixture is then neutralized with NaHCO$_3$ solution, dried and freed of solvent. The condensate is capable of flowing and is obtained in a yield of 97% of the theoretical value.

PREPARATION EXAMPLE 9

Co-Hydrolysis of the Product from Preparation Example 7 with TMOS 10.8 g (0.02 mol) of the compound from preparation example 7 are reacted with 0.8 g (0.005 mol) tetramethylorthosilicate and agitated in 50 ml acetic ester with 1.4 g (0.08 mol) water (added as 0.1 M HCl) for 36 hours at 36° C. The solution is neutralized by means of NaHCO₃ solution, dried and freed of solvent. The yield of viscose condensate is 96% of the theoretical value.

PREPARATION EXAMPLE 10

Preparation of the Hydrosilylation Product from 1-(trimethoxysilylethyl)-1,1,3,3-tetramethyldisiloxane with Vinyl Norbornene

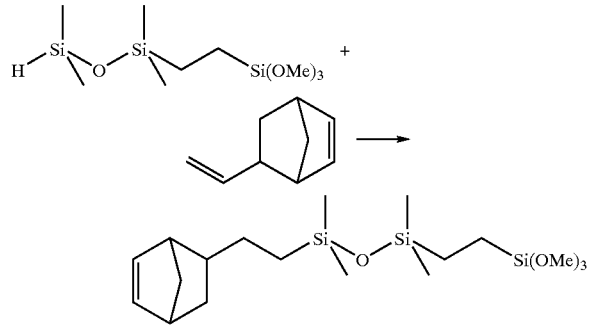

1-(trimethoxysilylethyl)-1,1,3,3-tetramethyldisiloxane was obtained from 1,1,3,3-tetramethyldisiloxane and vinyltrimethoxysilane according to J. V. Crivello and Daoshen Bi (J. Polym. Sci A 31 (1993) 3121).

14.1 g (0.05 mol) 1-(trimethoxysilylethyl)-1,1,3,3-tetramethyldisiloxane are heated to 100° C. in 100 ml dry toluene under inert gas with 5 mg polymer-bound Wilkinson catalyst and 6.0 g (0.05 mol) vinyl norbornene. After four hours, the vinyl absorptions in the ¹H-NMR spectrum have vanished. The reaction mixture is left to cool, filtered from the catalyst and the solvent drawn off under reduced pressure.

A colourless, low-viscosity oil remains. The yield is 98% of the theoretical value.

PREPARATION EXAMPLE 11

Hydrolysis and Condensation of the Product from Preparation Example 10

8.1 g (0.02 mol) of the compound from preparation example 10 are agitated with 1.1 g (0.06 mol) water (added as 0.1 M HCl) in 50 ml acetic ester for 24 hours at 40° C. The reaction mixture is then neutralized with NaHCO₃ solution, dried and freed of solvent. The condensate is capable of flowing and is obtained in a yield of 96% of the theoretical value.

PREPARATION EXAMPLE 12

Co-Hydrolysis of the Product from Preparation Example 10 with TMOS 8.1 g (0.02 mol) of the compound from preparation example 10 are mixed with 0.8 g (0.05 mol) tetramethylorthosilicate and agitated in 50 ml acetic ester with 1.4 g (0.08 mol) water (added as 0.1 M HCl) for 36 hours at 36° C. The solution is neutralized by means of NaHCO₃ solution, dried and freed of solvent. The yield of viscose condensate is 95% of the theoretical value.

PREPARATION EXAMPLE 13

Preparation of the Hydrosilylation Product of 1-(methyldimethoxysilylethyl)-1,1,3,3-tetramethyldisiloxane with Trimethylolpropanetriacrylate

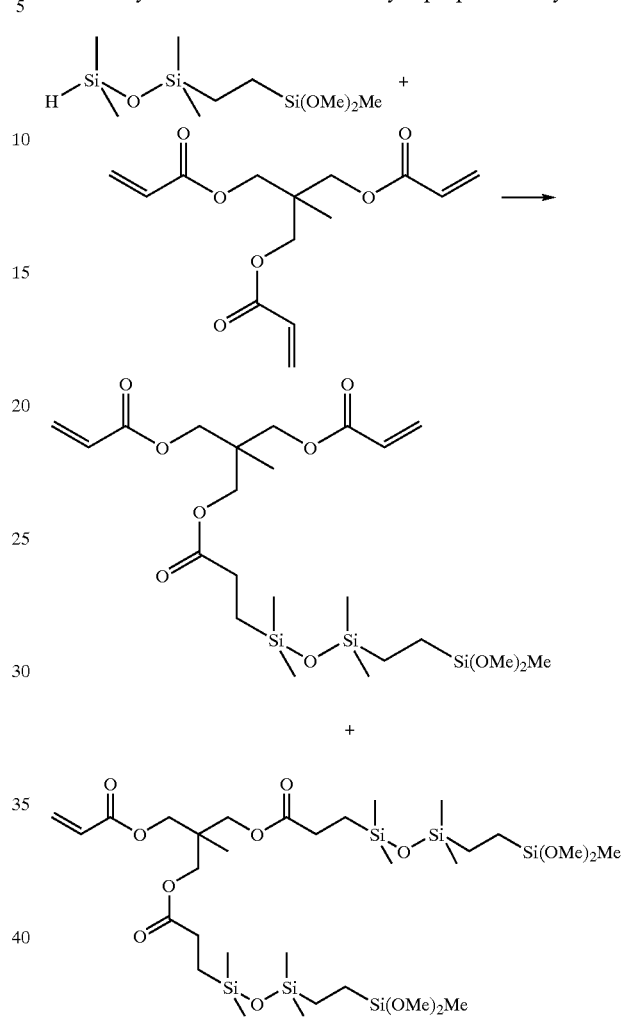

1-(methyldimethoxysilylethyl)-1,1,3,3-tetramethyldisiloxane was obtained analogously to J. V. Crivello and Daoshen Bi (J. Polym. Sci A 31 (1993) 3121) from 1,1,3,3-tetramethyldisiloxane and vinylmethyldimethoxysilane in a yield of 67% of the theoretical value.

8.0 g (0.03 mol) 1-(methyldimethoxysilylethyl)-1,1,3,3-tetramethyldisiloxane are heated to 100° C. in 100 ml dry toluene under inert gas with 5 mg polymer-bound Wilkinson catalyst and 14.4 g (0.05 mol) trimethylolpropanetriacrylate. After four hours, the vinyl absorptions in the ¹H-NMR spectrum have vanished. The reaction mixture is left to cool, filtered off from the catalyst and the solvent drawn off under reduced pressure.

A colourless, low-viscosity oil remains. The yield is 98% of the theoretical value.

PREPARATION EXAMPLE 14

Hydrolysis and Condensation of the Product from Preparation Example 13

7.5 g (0.01 mol, relative to the dimethoxysilyl content) of the compound from preparation example 13 are agitated with 0.4 g (0.02 mol) water (added as 0.1 M HCl) in 50 ml acetic ester for 24 hours at 40° C. The reaction mixture is then neutralized with NaHCO₃ solution, dried and freed of solvent. The condensate is capable of flowing and is obtained in a yield of 96% of the theoretical value.

PREPARATION EXAMPLE 15

Co-Hydrolysis of the Product from Preparation Example 13 with TMOS 7.5 g (0.01 mol relative to the dimethoxysilyl content) of the compound from preparation example 13 are mixed with 0.005 mol tetramethylorthosilicate and agitated in 50 ml acetic ester with 0.7 g (0.04 mol) water (added as 0.1 M HCl) for 36 hours at 36° C. The solution is neutralized by means of NaHCO₃ solution, dried and freed of solvent. The yield of viscose condensate is 95% of the theoretical value.

What is claimed is:

1. A method for preparing silicic acid polycondensates or silicic acid heteropolycondensates comprising hydrolytically condensing one or more hydrolytically condensable compounds of silicon, said hydrolytically condensable compound optionally comprising one or more elements selected from the group consisting of B, Al, P, Sn, Pb, the transition metals, the lanthanides and the actinides, said condensable compound optionally comprising precondensates of the compound; the reaction optionally comprising one or more of (i) a catalyst, (ii) a solvent, (iii) an ionically polymerizable compound and (iv) a free-radical polymerizable compound; wherein 5 to 100% mol % based on monomeric compounds of the hydrolytically condensable compounds are silanes of the general formula I:

(I)

in which:

B is a mono- to tetravalent, straight-chained or branched organic radical with at least one C=C double bond and 4 to 50 carbon atoms;

X is hydrogen, halogen, hydroxy, alkoxy, acyloxy, alkylcarbonyl, alkoxycarbonyl or NR"₂;

R is alkyl, alkenyl, aryl, alkylaryl or arylalkyl;

R' is alkylene, alkenylene, arylene, arylenealkylene or alkylenearylene having 2 to 10 carbon atoms, these radicals being able to be interrupted by oxygen and sulphur atoms or by amino groups;

R' is hydrogen, alkyl or aryl;

U is an inorganically modified organic radical comprising a siloxane or carbosiloxane framework having atoms that are silicon or germanium or a carbosilane framework having at least one atom that is silcon or germanium, said framework having 1 to 15 C atoms and up to 5 additional heteroatoms that are O, S or N;

A is C(=O)O, OC(=O)O, C(=O), O, S, C(=O)NR", OC(=O), or NR"(=O);

a = 1, 2 or 3;
b = 0, 1 or 2;
a + b = 3;
c = 1, 2, 3 or 4; and
d = 0 or 1.

2. The method of claim 1, wherein

B is a mono- to tetravalent, straight-chained or branched organic radical with at least one C=C double bond and 4 to 30 carbon atoms;

X is hydrogen, halogen, hydroxy, alkoxy, acyloxy or alkylcarbonyl;

R is alkyl, alkenyl or aryl;

R' is alkylene, alkenylene, arylene, arylenealkylene or alkylenearylene having 2 to 5 carbon atoms, these radicals being able to be interrupted by oxygen and sulphur atoms or by amino groups;

A is C(=O)O, OC(=O)O, C(O), 0, OC(=O);

U is an inorganically modified organic radical comprising a siloxane or carbosiloxane framework having atoms that are silicon or germanium or a carbosilane framework having at least one atom that is silcon or germanium, said framework having 1 to 15 C atoms and up to 5 additional heteroatoms that are O or N;

a = 1, 2 or 3;
b = 0, 1 or 2;
a + b = 3;
c = 1, 2, 3 or 4; and
d = 0 or 1.

3. The method according to claim 1, wherein the reaction mixture further comprises one or more compounds of the general formula VI, optionally in precondensed form, as an additional hydrolytically condensable compound of silicon:

(VI)

in which

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R" is hydrogen, alkyl or aryl;

R¹⁰ is alkylene or alkenylene, these radicals being able to be interrupted by oxygen or sulphur atoms or —NH groups;

Z' is halogen or an optionally substituted amino, amide, aldehyde, alkylcarbonyl, carboxy, mercapto, cyano, alkoxy, alkoxycarbonyl, sulfonic acid, phosphoric acid, acryloxy, methacryloxy, epoxy or vinyl group;

e = 0, 1, 2 or 3; and
f = 0, 1, 2 or 3, with e + f = 1, 2 or 3.

4. The method according to claim 3, in which

X is hydrogen, halogen, hydroxy, alkoxy, acyloxy or alkylcarbonyl; and

R is alkyl, alkenyl or aryl.

5. The method according to claim 2, wherein the reaction mixture further comprises one or more compounds of the general formula VI, optionally in precondensed form, as an additional hydrolytically condensable compound of silicon:

(VI)

in which

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R" is hydrogen, alkyl or aryl;

R¹⁰ is alkylene or alkenylene, these radicals being able to be interrupted by oxygen or sulphur atoms or —NH groups;

Z' is halogen or an optionally substituted amino, amide, aldehyde, alkylcarbonyl, carboxy, mercapto, cyano, alkoxy, alkoxycarbonyl, sulfonic acid, phosphoric acid, acryloxy, methacryloxy, epoxy or vinyl group;

| | |
|---|---|
| e = | 0, 1, 2 or 3; and |
| f = | 0, 1, 2 or 3, with e + f = 1, 2 or 3. |

6. The method according to claim 5, in which

X is hydrogen, halogen, hydroxy, alkoxy, acyloxy or alkylcarbonyl; and

R is alkyl, alkenyl or aryl.

7. The method according to claim 1, in which the reaction comprises at least one compound the general formula VIII, optionally in precondensed form, as an additional hydrolytically condensable compound of silicon:

$$Y_n SiX_m R_{4-(n+m)} \quad (VIII)$$

in which

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R" is hydrogen, alkyl or aryl;

Y is a substituent that comprises a substituted or unsubstituted 1,4,6-trioxaspiro-[4,4]-nonane radical;

| | |
|---|---|
| n = | 1, 2 or 3; and |
| m = | 1, 2 or 3, and n + m ≤ 4. |

8. The method according to claim 7, in which

| | |
|---|---|
| X = | hydrogen, halogen, hydroxy, alkoxy, acyloxy or alkylcarbonyl; and |
| R = | alkyl, alkenyl or aryl. |

9. The method according to claim 1, wherein one or more aluminium, titanium or zirconium compounds, soluble in the reaction medium, of the formula:

$$AlR° \text{ or } MX_y R_z$$

are used, optionally in precondensed form, as an additional hydrolytically condensable compound in which M is titanium or zirconium;

the radicals R, R° and X are the same or different;

R° is halogen, hydroxy, alkoxy or acyloxy;

y=1, 2, 3 or 4;

z=0, 1, 2 or 3; and

X is hydrogen, halogen, hydroxy, alkoxy, acyloxy, alkylcarbonyl, alkoxycarbonyl or NR" 2;

R is alkyl, alkenyl, aryl, alkylaryl or arylalkyl; and

R" is hydrogen, alkyl or aryl.

10. The method according to claim 9, in which

X is hydrogen, halogen, hydroxy, alkoxy, acyloxy or alkylcarbonyl; and

R is alkyl, alkenyl or aryl.

11. The method according to claim 10, in which y=2, 3 or 4.

12. The method according to claim 9, in which z=0, 1 or 2.

13. The method according to claim 12, in which y=2, 3 or 4.

14. The method according to claim 1, wherein one or more initiators are added to the polycondensate, and the polycondensate is then cured thermally, photochemically, in a covalent-nucleophilic manner or by redox-induction.

15. The process according to claim 1, wherein the reaction mixture further comprises one or more compounds of the general formula IX, optionally in precondensed form, as at least one condensable compound of silicon:

$$G\{A\!-\!(Z)_d\!-\!R^{20}(R^{21})\!-\!R'\!-\!SiX_a R_b\}_c \quad (IX)$$

in which:

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R" is hydrogen, alkyl or aryl; and

G is a straight-chained or branched organic radical with at least one C=C double bond and 4 to 50 carbon atoms;

d=1;

A is O, S or NH;

z is C=O;

$R^{20}$ is alkylene, arylene or alkylenearylene comprising 1 to 10 carbon atoms, and optionally interrupted by one or more atom of oxygen or sulfur or by one or more amino group;

$R^{21}$ is COOH; or

G is a straight-chained or branched organic radical with at least one C=C double bond and 4 to 50 carbon atoms;

d=1

A is O, S, or NH;

Z is C=O;

$R^{20}$ is alkylene, arylene or alkylenearylene comprising 1 to 10 carbon atoms, and optionally interrupted by one or more atom of oxygen or sulfur or by one or more amino groups;

$R^{21}$ is H; or

G is a straight-chained or branched organic radical with at least one C=C double bond and 4 to 50 carbon atoms;

d=0

A is O, S, NH or COO;

$R^{20}$ is alkylene, arylene or alkylenearylene comprising 1 to 10 carbon atoms, and optionally interrupted by one or more atom of oxygen or sulfur or by one or more amino group;

$R^{21}$ is OH; or

G is a straight-chained or branched organic radical with at least one C=C double bond and 4 to 50 carbon atoms;

d=1;

A is S;

Z is C=O;

$R^{20}$ is N;

$R^{21}$ is H; or

G is a straight-chained or branched organic radical with at least one C=C double bond and 4 to 50 carbon atoms;

d=1;

A is O, S, NH or COO;

Z is CHR, with R being H, alkyl, or alkylaryl;

$R^{20}$ is alkylene, arylene or alkylenearylene comprising 1 to 10 carbon atoms, and optionally interrupted by one or more atom of oxygen or sulfur or by one or more amino group;

$R^{21}$ is OH; and

| | |
|---|---|
| a = | 1, 2 or 3; |
| b = | 0, 1 or 2; |
| a + b = | 3; |
| c = | 1, 2, 3 or 4. |

16. The method of claim 15, in which

| | |
|---|---|
| X = | hydrogen, halogen, hydroxy, alkoxy, acyloxy or alkylcarbonyl; and |
| R = | alkyl, alkenyl or aryl. |

17. A polymer made by the process of claim 1.

18. A dental filling material, dental cement, dental crown, dental bridge, dental facing material, dental lacquer, dental sealer, dental adhesion promoter, dental primer or dental bonder comprising a polymer made by the process of any one of claims 3–6.

19. A method for preparing silicic acid polycondensates or silicic acid heteropolycondensates comprising hydrolytically condensing one or more hydrolytically condensable compounds of silicon, said hydrolytically condensable compound optionally comprising one or more elements selected from the group consisting of B, Al, P, Sn, Pb, the transition metals, the lanthanides and the actinides, said condensable compound optionally comprising precondensates of the compound; the reaction optionally comprising one or more of (i) a catalyst, (ii) a solvent, (iii) an ionically polymerizable compound and (iv) a free-radical polymerizable compound; wherein 5 to 100% mol % based on monomeric compounds of the hydrolytically condensable compounds are silanes of the general formula I:

B{(A)$_d$—R'—U—R'—SiX$_a$R$_b$}$_c$ (I)

in which:

B is a mono- to tetravalent, straight-chained or branched organic radical with at least one C=C double bond and 4 to 50 carbon atoms;

X is hydrogen, halogen, hydroxy, alkoxy, acyloxy, alkylcarbonyl, alkoxycarbonyl or NR''2;

R is alkyl, alkenyl, aryl, alkylaryl or arylalkyl;

R' is alkylene, alkenylene, arylene, arylenealkylene or alkylenearylene having 2 to 10 carbon atoms, these radicals being able to be interrupted by oxygen and sulphur atoms or by amino groups;

R'' is hydrogen, alkyl or aryl;

U is an inorganically modified organic radical comprising a siloxane or carbosiloxane framework having at least two atoms that are silicon or germanium or a carbosilane framework having at least one atom that is silcon or germanium, said framework having 1 to 15 C atoms and up to 5 additional heteroatoms that are O, S or N;

A is C(=O)O, OC(=O)O, C(=O), O, S, C(=O)NR'', OC(=O), or NR''C(=O);

| | |
|---|---|
| a = | 1, 2 or 3; |
| b = | 0, 1 or 2; |
| a + b = | 3; |
| c = | 1, 2, 3 or 4; and |
| d = | 0 or 1; | wherein an ionically polymerizable compound or a free-radically polymerizable compound is present in the reaction.

20. A method for preparing silicic acid polycondensates or silicic acid heteropolycondensates comprising hydrolytically condensing one or more hydrolytically condensable compounds of silicon, said hydrolytically condensable compound optionally comprising one or more elements selected from the group consisting of B, Al, P, Sn, Pb, the transition metals, the lanthanides and the actinides, said condensable compound optionally comprising precondensates of the compound; the reaction optionally comprising one or more of (i) a catalyst, (ii) a solvent, (iii) an ionically polymerizable compound and (iv) a free-radical polymerizable compound; wherein 5 to 100% mol % based on monomeric compounds of the hydrolytically condensable compounds are silanes of the general formula I:

B{(A)$_d$—R'—U—R'—SiX$_a$R$_b$}$_c$ (I)

in which:

B is a mono- to tetravalent, straight-chained or branched organic radical with at least one C=C double bond and 4 to 30 carbon atoms;

X is hydrogen, halogen, hydroxy, alkoxy, acyloxy or alkylcarbonyl;

R is alkyl, alkenyl or aryl;

R' is alkylene, alkenylene, arylene, arylenealkylene or alkylenearylene having 2 to 5 carbon atoms, these radicals being able to be interrupted by oxygen and sulphur atoms or by amino groups;

A is C(=O)O, OC(=O)O, C(O), O, OC(=O);

U is an inorganically modified organic radical comprising a siloxane or carbosiloxane framework having two atoms that are silicon or germanium or a carbosilane framework having at least one atom that is silcon or germanium, said framework having 1 to 15 C atoms and up to 5 additional heteroatoms that are O or N;

| | |
|---|---|
| a = | 1, 2 or 3; |
| b = | 0, 1 or 2; |
| a + b = | 3; |
| c = | 1, 2, 3 or 4; and |
| d = | 0 or 1; | wherein an ionically polymerizable compound or a free-radically polymerizable compound is present in the reaction.

21. A method for preparing a polymer comprising radical polymerizing one or more compounds that comprise at least one C=C double bond and optionally other radically polymerizable compounds;

the reaction mixture optionally further comprising one or more ionically polymerizable compounds and the process optionally further comprising ionically polymerizing said ionically polymerizable compounds by one or more of heating, irradiating the reaction with electromagnetic radiation, a redox-induction or a covalent-nucleophilic reaction, the reaction mixture optionally further comprising one or more hydrolytically condensable compounds of silicon and optionally other elements selected from the group consisting of B, Al, Sn, Pb, the transition metals, the lanthanides and the actinides, and/or precondensates derived from said hydrolytically condensable compounds and the process further optionally comprising hydrolytically condensing said hydrolytically condensable compounds of silicon;

the reaction mixture still further optionally comprising one or more initiators and/or a solvent;

wherein 5 to 100 mol % based on monomeric compounds are selected from condensates of silanes of formula I:

in which:

B is a mono- to tetravalent, straight-chained or branched organic radical with at least one C=C double bond and 4 to 50 carbon atoms;

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R' is alkylene, alkenylene, arylene, arylenealkylene or alkylenearylene having 2 to 10 carbon atoms, these radicals being able to be interrupted by oxygen and sulphur atoms or by amino groups;

R" is hydrogen, alkyl or aryl;

U is an inorganically modified organic radical comprising a siloxane or carbosiloxane framework having two atoms that are silicon or germanium or a carbosilane framework having at least one atom that is silcon or germanium, said framework having 1 to 15 C atoms and up to 5 additional heteroatoms that are O, S or N;

A is C(=O)O, OC(=O)O, C(=O), O, S, C(=O)NR", OC(=O), or NR"C(=O);

| |
|---|
| a = 1, 2 or 3; |
| b = 0, 1 or 2; |
| a + b = 3; |
| c = 1, 2, 3 or 4; and |
| d = 0 or 1. |

22. The method of claim 21, wherein

B is a mono- to tetravalent, straight-chained or branched organic radical with at least one C=C double bond and 4 to 30 carbon atoms;

X is hydrogen, halogen, hydroxy, alkoxy, acyloxy or alkylcarbonyl;

R is alkyl, alkenyl or aryl;

R' is alkylene, alkenylene, arylene, arylenealkylene or alkylenearylene having 2 to 5 carbon atoms, these radicals being able to be interrupted by oxygen and sulphur atoms or by amino groups;

A is C(=O)O, OC(=O)O, C(O), O or OC(=O);

U is an inorganically modified organic radical comprising a siloxane or carbosiloxane framework having at least two atoms that are silicon or germanium or a carbosilane framework having at least one atom that is silcon or germanium, said framework having 1 to 15 C atoms and up to additional heteroatoms that are O or N;

| |
|---|
| a = 1, 2 or 3; |
| b = 0, 1 or 2; |
| a + b = 3; |
| c = 1, 2, 3 or 4; and |
| d = 0 or 1. |

23. The method of claim 22, in which one or more silanes of the general formula VIII are used as cationically polymerizable compounds:

$$Y_n SiX_m R_{4-(n+m)} \quad (VIII)$$

in which

X is hydrogen, halogen, hydroxy, alkoxy, acyloxy, alkylcarbonyl, alkoxycarbonyl or NR"2;

R is alkyl, alkenyl, aryl, alkylaryl or arylalkyl;

R" is hydrogen, alkyl or aryl;

Y is a substituent that comprises a substituted or unsubstituted 1,4,6-trioxaspiro-[4,4]-nonane radical;

| | |
|---|---|
| n = | 1, 2 or 3; and |
| m = | 1, 2 or 3, and n + m is less than or equal to 4. |

24. The method according to claim 21, wherein the reaction mixture comprises at least one hydrolytically condensable compound of silicon and optionally other elements from the group consisting of B, Al, Sn, Pb, the transition metals, the lanthanides and the actinides, and/or precondensates derived from said hydrolytically condensable compound, and the process further comprises a step of hydrolytically condensing said at least one hydrolytically condensable compound.

25. The method according to claim 22, wherein the reaction mixture comprises at least one hydrolytically condensable compound of silicon and optionally other elements from the group consisting of B, Al, Sn, Pb, the transition metals, the lanthanides and the actinides, and/or precondensates derived from said hydrolytically condensable compound, and the process further comprises a step of hydrolytically condensing said at least one hydrolytically condensable compound.

26. according to claim 23, wherein the reaction mixture comprises at least one hydrolytically condensable compound of silicon and optionally other elements from the group consisting of B, Al, Sn, Pb, the transition metals, the lanthanides and the actinides, and/or precondensates derived from said hydrolytically condensable compound, and the process further comprises a step of hydrolytically condensing said at least one hydrolytically condensible compound.

27. The method according to claim 21, in which the reaction mixture comprises one or more compounds of the general formula VI, optionally in precondensed form, as at least one hydrolytically condensable compound of silicon:

in which
- X is hydrogen, halogen, hydroxy, alkoxy, acyloxy, alkylcarbonyl, alkoxycarbonyl or $NR''_2$;
- R is alkyl, alkenyl, aryl, alkylaryl or arylalkyl;
- R'' is hydrogen, alkyl or aryl;
- $R^{10}$ is alkylene or alkenylene, these radicals being able to be interrupted by oxygen or sulphur atoms or —NH groups;
- Z' is halogen or an optionally substituted amino, amide, aldehyde, alkylcarbonyl, carboxy, mercapto, cyano, alkoxy, alkoxycarbonyl, sulfonic acid, phosphoric acid, acryloxy, methacryloxy, epoxy or vinyl group;

| | |
|---|---|
| e = | 0, 1, 2 or 3; and |
| f = | 0, 1, 2 or 3; with e + f = 1, 2 or 3. |

\* \* \* \* \*

UNITED STATES PATENT AND TRADEMARK OFFICE
CERTIFICATE OF CORRECTION

PATENT NO. : 6,852,822 B1
APPLICATION NO. : 10/031612
DATED : February 8, 2005
INVENTOR(S) : Peter Bissinger It is certified that error appears in the above-identified patent and that said Letters Patent is hereby corrected as shown below:

Column 4
Line 48, delete "-(A)$_n$" and insert -- -(A)$_d$ --, therefor.

Column 7
Line 26, under (Below Structure), delete "Si(Me)$_2$;" and insert -- Si(Me)$_2$-; --, therefor.
Line 37, delete "(CH2)$_n$" and insert -- (CH$_2$)$_n$ --, therefor.
Line 39, delete "(OCH3)" and insert -- (OCH$_3$) --, therefor.
Line 62, delete "(OC2H$_5$)" and insert -- (OC$_2$H$_5$) --, therefor.

Column 9
Line 22, delete "DE-C4" and insert -- DE-C-4 --, therefor.
Line 30, delete "DE-A4" and insert -- DE-A-4 --, therefor.

Column 11
Line 6, delete "N H$_2$" and insert -- NH$_2$ --, therefor
Line 33, delete "Y+a" and insert -- Y = a --, therefor.
Line 37, delete "m=1, 3 or 3" and insert -- m=1, 2 or 3 --, therefor.
Line 37, delete "or" before "with".
Line 40, delete "DE-C4" and insert -- DE-C-4 --, therefor.

Column 15
Line 26, delete "DE-A4" and insert -- DE-A-4 --, therefor.
Line 30, delete "DE-A4" and insert -- DE-A-4 --, therefor.

Column 21
Line 44, in Claim 1, delete "R'" and insert -- R" --, therefor.
Line 46, in Claim 1, after "having" insert -- two --.
Line 52, in Claim 1, delete "NR"(=O);" and insert -- NR"C (=O); --, therefor.

Column 22
Line 8, in Claim 2, after "having" insert -- two --.

Column 23
Line 24, in Claim 15, before "is" delete "z" and insert -- Z --, therefor.

Column 25
Line 51, in Claim 19, delete "NR"2;" and insert -- NR"$_2$; --, therefor.

UNITED STATES PATENT AND TRADEMARK OFFICE
CERTIFICATE OF CORRECTION

PATENT NO. : 6,852,822 B1
APPLICATION NO. : 10/031612
DATED : February 8, 2005
INVENTOR(S) : Peter Bissinger It is certified that error appears in the above-identified patent and that said Letters Patent is hereby corrected as shown below:

Column 27
Line 67, in Claim 22, insert -- 5 -- before "additional".

Column 28
Line 53, in Claim 26, insert -- The method -- before "according".

Column 30
Line 7, in Claim 27, before "with" delete ";" and insert -- , --, therefor.

Signed and Sealed this

Twentieth Day of May, 2008

JON W. DUDAS
*Director of the United States Patent and Trademark Office*